(12) United States Patent
Beigel et al.

(10) Patent No.: US 8,778,238 B2
(45) Date of Patent: Jul. 15, 2014

(54) FLUID CONDUITS WITH MOLDED PLASTIC PART

(75) Inventors: Bertram Beigel, Karlsruhe (DE);
Jochen Mueller, Karlsruhe (DE);
Tilmann Rogge, Heldelberg (DE)

(73) Assignee: Agilent Technologies, Inc., Santa Clara, CA (US)

(*) Notice: Subject to any disclaimer, the term of this patent is extended or adjusted under 35 U.S.C. 154(b) by 1346 days.

(21) Appl. No.: 11/989,117

(22) PCT Filed: Jul. 19, 2005

(86) PCT No.: PCT/EP2005/053487
§ 371 (c)(1),
(2), (4) Date: Sep. 1, 2009

(87) PCT Pub. No.: WO2007/009493
PCT Pub. Date: Jan. 25, 2007

(65) Prior Publication Data
US 2010/0000927 A1    Jan. 7, 2010

(51) Int. Cl.
*B29D 11/00* (2006.01)
(52) U.S. Cl.
USPC .......... 264/1.25; 264/261; 264/263; 264/267
(58) Field of Classification Search
USPC ................. 264/1.25, 261, 263, 267
See application file for complete search history.

(56) References Cited

U.S. PATENT DOCUMENTS

| | | | |
|---|---|---|---|
| 2,425,831 A | 8/1947 | Rozanek | |
| 3,469,579 A | 9/1969 | Hubert | |
| 3,734,594 A * | 5/1973 | Trambarulo | 385/70 |
| 4,116,655 A * | 9/1978 | Lewis | 65/401 |
| 4,178,067 A * | 12/1979 | Johnson et al. | 385/95 |
| 5,013,495 A * | 5/1991 | Noba et al. | 264/1.25 |
| 5,115,552 A | 5/1992 | Mattson et al. | |
| 5,240,537 A | 8/1993 | Bodicky et al. | |
| 5,614,154 A | 3/1997 | Glatz et al. | |
| 6,974,557 B1 * | 12/2005 | Webler et al. | 264/443 |
| 2003/0030277 A1 | 2/2003 | Morohoshi et al. | |
| 2003/0102671 A1 | 6/2003 | Fritze | |

FOREIGN PATENT DOCUMENTS

| EP | 0 363 953 A | 4/1990 |
|---|---|---|
| FR | 2 803 558 A | 7/2001 |

OTHER PUBLICATIONS

International Search Report Written Opinion of the ISA, Jul. 19, 2005.

* cited by examiner

*Primary Examiner* — Joseph S Del Sole
*Assistant Examiner* — David N Brown, II (57) ABSTRACT

A method of providing a conduit (5, 7, 49, 51 93, 129, 131, 151, 231, 233, 259) adapted for conducting a medium, with a functional element. The functional element is adapted for at least one of: coupling, connecting, sealing, fixing, adjusting, aligning, receiving, protecting, and positioning the conduit. A part, comprising a plastic material, is plastified and molded within a forming tool for shaping the form of the functional element and for attaching the functional element to the conduit.

13 Claims, 8 Drawing Sheets

FLUID CONDUITS WITH MOLDED PLASTIC PART

This application is the National Stage of International Application No. PCT/EP2005/053487, filed on 19 Jul. 2005 which designated the United States of America, and which international application was published as Publication No. WO 2007/009493.

BACKGROUND ART

The present invention relates to providing conduits.

Conduits provided with functional elements are used, for example, in liquid chromatography. Different kinds of conduits adapted for conducting a medium, for example, light and/or a fluid, have to be connected for bringing them in communication. A flow cell, for example, can comprise at least one fluid conduit and at least one light guide communicating with each other. The conduits can be provided with functional elements, for example, threads or standardized fittings, for bringing them in communication.

U.S. Pat. No. 5,614,154 (by the same applicant) discloses a connecting capillary for analytical measuring technology, in particular a fused silica capillary, wherein the glass capillary is surrounded at least its end regions by a sheath of poly-etheretherketone (PEEK) or a PEEK-derivative.

WO 2005015162 shows a terminal for placing fluidic conduits in communication with a conduit comprising a proximal end inserted into a housing with a bore having been back-filled with a liquefied thermoplastic polymer.

DISCLOSURE

It is an object of the invention to provide an improved conduit. The object is solved by the independent claims. Further embodiments are shown by the dependent claims.

According to embodiments of the present invention, a method of providing conduits with at least one functional element is suggested. The conduits are adapted for conducting a medium, for example, a fluid or light. The functional element is adapted for connecting, sealing, positioning, and/or protecting the conduits. Embodiments may comprise one or more of the following: A part is plastified and molded within a forming tool for forming or better for shaping the form of the functional element and for fixing the functional element with or better for attaching the functional element to a conduit. The part comprises a plastic material. Advantageously, this technique enables sealing, connecting, positioning of said functional element on very fragile parts and very small sizes, were common techniques fail, for example, microfluidic conduits, light guides, capillaries, or alike. Advantageously, the forming tool can form the shape, for example the outer shape, of the functional element to a desired shape with a good dimensional stability and a high reproducibility. Additionally, close tolerances can be held or maintained, for example, by exactly adjusting the process parameters like the temperature and the detention time within the forming tool. Advantageously the forming tool can be used very often. In other embodiments, it is possible, to design a single-use forming tool. By this, the step of demolding can be dropped and, for example, functional elements comprising non-demoldable shapes can be realized.

The part can be realized as a pre-formed part, wherein the shape of the pre-formed part is adapted to the shape of the conduit and of the forming tool for optimizing the transforming process and the connection of the conduit and the functional part. The pre-formed part can be plastified by heating the plastic material above or beyond the softening temperature and bringing it in its softening range for making it soft and pliable. Advantageously, the plastified plastic material can be evenly formed to the outer surface of the conduit. This enables a homogenous force distribution across the surface of the conduit. Besides this, the mechanical stress after forming the functional element can be reduced.

In embodiments, the pre-formed part can comprise two or more component parts, wherein said component parts are joined to each other by the step of transforming the pre-formed part to the functional element. For improving said joint connection, the component parts of the pre-formed part can be separated by a foil enabling an adhesive-bonded joint between the component parts.

In embodiments, firstly, the forming tool is equipped at least partly with the at least one conduit and with the at least one pre-formed part. The pre-formed part comprises the plastic material and is adapted to be formed for producing the functional element. Advantageously, the pre-formed part can be easily produced with a relative low exactness, for example, by extruding, injection molding, or alike and is thus cost effective. The process supports also pre-formed parts already connected to a conduit, for example, pre-fabricated PEEK-capillaries or PEEK-fibers. Advantageously, such conduits are commercially available and can comprise, for example, a PEEK-coating and/or connector. The PEEK-coating and/or connector can fulfill the same function as said separate pre-formed part. By this, the forming tool can be loaded simply just with the conduit comprising the pre-formed coating comprising, for example, PEEK.

Advantageously, the formed functional elements fulfill close tolerances. The dimensional consistency is guaranteed by forming the pre-formed part by the forming tool. One forming tool can be used for different insets, different types of conduits, for example, light guides, fluid conduits, capillaries, glass capillaries, fused silica capillaries, rods, bars, needles, syringes or alike.

Before forming the functional element, an outer surface of the conduit can be at least partly surrounded with the pre-formed part. After forming, the functional element can adhere to the outer surface of the conduit, for example, by frictional forces, shrink forces and/or a chemical bond. The functional element can realize a fluid tight sealing. For forming the functional element, the forming tool can be closed for exerting pressure on the softened pre-formed part.

The tool can be closed and heated together with the plastic material of the pre-formed part. Possibly, pressure can be exerted on the plastic material by thermal expanding the plastic material by heating it within the closed forming tool. Besides this, the pressure can be exerted by a moving piston of the forming tool. Due to the pressure, the plastic material can penetrate the surface structure of the outer surface. For this purpose, the outer surface can comprise a roughening. After forming, the forming tool can be opened. Possibly, the tool can be opened before cooling down the already formed functional element. By this, the production quantity per time unit can be increased. The step of cooling down the functional element to ambient temperature can be parallelized with the step of forming the next unit. Or, for adjusting, for example, a lower and/or exacter temperature gradient, the plastic material can be cooled down within the forming tool. The cooling down can also be forced actively by well known practices like air, or fluidic cooling of the parts, or surrounding parts, or with a thermocouple.

Advantageously, the plastic material can be shrunk on the outer surface of the conduit by cooling the plastic material down to ambient temperature. Advantageously, desired shrinking forces can be adjusted by varying the dimension of the functional element and/or the dimensions of the plastic material. Advantageously, for example, just a part or just the end of the conduit can be provided with the functional element shrunk onto the outer surface. For this purpose, just the part or just the end of the conduit can be inserted into the forming tool. After treating the pre-formed part, the forming tool can be removed.

Embodiments may comprise one or more of the following. The plastic material can be heated within the forming tool close to or above the melting temperature for bringing the plastic material to the softening range or for melting the plastic material. By this, a chemical bond between the outer surface and the plastic material is possible. For avoiding a similar chemical bond of the plastic material at the boundary point of the inner surface of the mold to the forming tool, one can choose a tooling material which will not cling together with the plastic material or the mold and/or the forming tool can be coated with an according release agent. By this, the demolding of the functional element is still possible.

The same chemical bond can be produced by heating the functional element at least partly above the melting temperature, for example, after molding, after removing, after molding and before opening the forming tool, or after cooling down the functional element to ambient temperature. The already formed functional element can be melted partly at a contact zone of the outer surface, for example, at the end of the conduit and the plastic material. Advantageously, the plastic material can be melted partly with a relative low temperature gradient before cooling down. The functional element can be melted partly at the contact zone by running a hot fluid, for example, a liquid such as oil or a gas, through the conduit and/or by inserting a heat source, for example, a heated metal pin. Advantageously, the thermal conduction can be increased by running the liquid or gas through the conduit. Consequently, the production time per piece can be reduced.

For optimizing the loading of the forming tool, the conduit can be provided with the pre-formed part before loading the forming tool The functional element can be realized, for example, as a fitting, a standardized fitting for example with a thread, a connector for permanent connections, and/or a coating for protecting the conduit. In further embodiments, the functional element can be realized as a limit stopper, rotation stopper, to aim at something, as an aligning part, as a forming key and/or more.

The functional element can comprise additional parts, for example a gold ring or ceramic ring or several balls, which are positioned within the tool prior to the forming process and which are fixed to the functional element within the forming process. After the forming process, the additional parts are coupled to the functional element. Advantageously, the additional parts have even better properties than the plastic material itself, for example, better durability, better tolerances, better temperature stability, better hardness, better sealing properties, better softness, magnetic or conductive properties depending on the application.

The functional element, for example, with the additional parts can be used to let the application know if a coupling is done or not, for example, a gold contact in one functional element as a male connector and two gold balls in the functional element as a female connector building a connecting bridge when put together, which can be electronically detected from the system.

The functional element formed with a key function, for example, can be used to avoid wrong or damaging coupling of fragile parts like optical fibers or alike, for example, forming shapes that only fit together within the wanted application if the connecting device has the correct counterpart.

The functional element can even build a locking device in a connector. For this purpose, for example, one element—for example the functional element—can comprise an undercut and the other element—for example the connector—can comprise a pin, bead, or another suited counterpart engaging the undercut to prevent from disconnecting.

Embodiments may comprise one or more of the following. Possibly, the forming tool can comprise two or more molds for forming, for example, two connectors to two conduits to be connected via a sleeve. For this purpose, a first connector can be formed to the outer surface of a first conduit and the sleeve and a second connector can be formed to the outer surface of a second conduit and the sleeve. The sleeve is adapted for at least partly surrounding the outer surfaces of the conduits.

The plastic material can be a thermoplastic material or compound, for example polyetheretherketone (PEEK), flouropolymeres for example perfluoroamines (PFA) or flourinated ethylen-propylen copolymer (FEP), duroplastic material or compound for example polyimide, LCP (liquid crystal polymers), and/or perfluoroamines (PFA), comprising advantageous material properties. For example, a high persistence against aggressive solvents and good properties for sealing. Additionally, the plastic material can be coated after forming with a sealing material, for example, with silicon, rubber, Teflon®, or alike.

Advantageously, the plastic material can also be a compound of metal with a thermoplastic material. For example the compound can be a magnetic material to fix one connector part to another, or the compound can be a conductive material to receive the heat for plastically softening or melting the plastic by induced current.

Further embodiments of the present invention relate to an arrangement of a coupling for bringing conduits in communication. The coupling comprises at least one conduit adapted for conducting a medium, for example, a fluid and/or light, and a functional element adapted for bringing the conduit in communication with another conduit, for example, coupling, connecting, sealing, fixing, adjusting, aligning, receiving, protecting, and/or positioning the conduit.

Embodiments may comprise one or more of the following. A first conduit is provided with a functional element adapted for bringing the conduit in communication with another conduit. The functional element is permanently fixed with the conduit by plastifying and molding the pre-formed part. The pre-formed part can be formed within a forming tool adapted for forming the functional element and for fixing the functional element with the conduit or better for shaping the form of the functional element and for attaching the functional element to the conduit.

The plastic material is in sealing contact with an outer surface of the conduit. For realizing an adhesive-bonded joint, the outer surface is provided with the sealing plastic material. Advantageously, the adhesive-bonded joint of the outer surface can be designed relatively small-sized due to the homogenous contact of the plastic material with the outer surface of the conduit. Said homogenous contact can be produced by plastifying and molding the pre-formed part. The plastic material softens completely by heating above the softening temperature. When cooling down, the material shrinks on or onto the outer surface of the conduit and the desired circumferential mechanical stress occurs. The mechanical stress causes desired sealing forces enhancing the fluid tightness of the contact between the plastic material and the outer surface of the conduit. Therefore, the plastic material comprises a higher thermal expansion than the material of the conduit; for example, the conduit comprises a glass capillary and the functional element PEEK. Therefore, the functional element is shrunk on the outer surface of the conduit and additional frictional forces for additionally stabilizing said adhesive-bonded joint occur.

Embodiments may comprise one or more of the following. The coupling can comprise a chemical bond between the outer surface and the plastic material. Such a chemical bond can be produced by melting the plastic material at least partly at a contact zone of the outer surface of the conduit and the functional element. Advantageously, this effect Improves the fluid tightness and can consequently be used to reduce the dimension of the functional element.

For sealing, the functional element surrounds the outer surface of the conduit at least partly, for example, circumferential and adjacent to an outlet of the conduit. Advantageously, the functional element can realize a fitting, for example, a standardized fitting for the conduit. The fitting can comprise a sealing surface comprising a coating adapted for sealing such as rubber, silicon, Teflon®, or alike. Advantageously, the fitting can be adapted for coupling the conduit with another conduit.

Embodiments may comprise one or more of the following. The functional element can be a coating adapted for protecting the conduit. Possibly, the fitting can be combined with the coating.

Embodiments may comprise one or more of the following. The functional element can be realized as a connector adapted for permanently or temporarily coupling at least two conduits. The connector part surrounds at least party and is fixed with an outer surface of a first conduit and/or an outer surface of a second conduit.

Advantageously, the outer surfaces of the two conduits are adjacent to each other. Therefore, the end of the first conduit can be inserted into an inner tube of the second conduit. The connector is shrunk circumferentially to the outer surfaces of the first and the second conduits. Therefore, the connector is frictionally connected with and/or chemical bonded with the outer surfaces and therefore fixes the first conduit with the second conduit. Advantageously, the two connected surfaces can be sealed with the connector, if necessary.

Embodiments may comprise one or more of the following. The coupling can comprise two connectors formed out of a first connector part and a second connector part. Each adapted for at least partly surrounding an outer surface of one conduit. Besides this, the coupling comprises a sleeve, wherein the first conduit is inserted into a first opening of the sleeve, and wherein the second conduit is inserted into a second opening of the sleeve. The outlets of the first and second conduits are facing each other within the sleeve. At the interfacial area of the outer surface of the sleeve and the outer surfaces of the first and second conduits, the coupling comprises a first and a second connector. The first connector surrounds the first conduit and the sleeve and the second connector surrounds the second conduit and the sleeve.

The connectors can be produced with a forming tool comprising two different molds, one mold for each connector. The connectors are each shrunk on the outer surfaces of the sleeve and the conduits and are in a sealing contact at the interfacial area of the sleeve and the outer surfaces of the conduits. More precisely, the two conduits are connected via the sleeve and sealed and fixed with each other by the first and the second connector. By this, two conduits with the same outer diameter can be connected via the two connectors. For connecting two conduits with different outer diameter the sleeve can comprise a step bore or multiple-step bore. The outer surface of the sleeve is adjacent to the outer surfaces of the first and second conduit and can therefore seal and connect the conduits with the sleeve. The outer surfaces of the first and second conduit face at least partly an inner surface of the sleeve. Possibly, the outer surfaces and the inner surface can realize a fit, for example, a press fit or a loose fit. A loose fit is advantageous for assembling the two conduits with the sleeve. A press fit is good for pre-connecting the sleeve and the conduits in a frictional manner and for avoiding an undesired separation of the pre-assembled parts.

Embodiments may comprise one ore more of the following. A variety of different conduits can be connected, for example, capillaries, glass capillaries, fused silica capillaries, light guides, and/or metal capillaries. The plastic material can be a high performance plastic material, such as polyeheretherketone (PEEK) fluoropolymers for example perfluoroamines (PFA) or fluorinated ethylene-propylene copolymer (FEP), a duroplastic material or compound for example polyimide or another thermoplastic material or compound matching the applications needs.

Further embodiments of the invention relate to a flow cell adapted for analyzing a fluid. The flow cell comprises a coupling with a formed functional element comprising a plastic material that was at least partly plastified.

Further embodiments of the invention relate to a fluid separation system with a fluid delivery system, a separation device for separating components of the fluid delivered by the fluid delivery system, and a flow cell comprising a coupling with a functional element as described above.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

Figure 1:
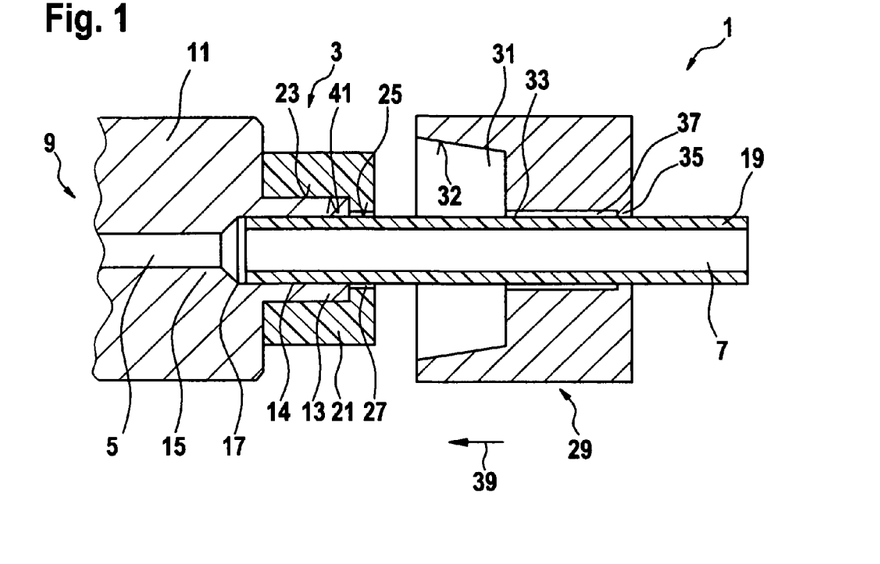
FIG. 1 shows a longitudinal view of an arrangement with a pre-fabricated coupling being part of the arrangement with two conduits and a pre-formed connector part together with an opened forming tool.

FIG. 1 shows a longitudinal view of an arrangement 1 of a pre-fabricated coupling 3 adapted for coupling a first fluid conduit 5 with a second fluid conduit 7. The first fluid conduit 5 can be coupled, for example, to a partly shown analytical separation column 9. In further embodiments, the conduit can be included in the column 9. As shown in FIG. 1, the column end 9 can be formed as an adapter fitting 11 adapted for receiving the fluid conduit 7. Therefore, the adapter fitting 11 can comprise a sheathing 13 with an inner tube or hole 14 comprising an inner surface adapted for receiving the second fluid conduit 7. The inner surface of the inner tube 14 of the sheathing 13 can be realized by a multiple-step bore 15 of the adapter fitting 11. The diameter of the multiple-step bore 15 of the adapter fitting 11 is reduced at a step 17 from the outer diameter of the second fluid conduit 7 to the inner diameter of an inner tube 19 of the second fluid conduit 7. By this, the coupling 3 realizes a connection for the fluid conduits 5 and 7 to a continuous fluid conduit comprising a substantially constant inner diameter. For avoiding any dead volume, the step 17 can comprise a flank adapted to the shape of the end of the second fluid conduit 7. Consequently, the end of the second fluid conduit 7 can be installed flush with the flank of the step 17 and bear against the flank of the step 17. The flank of the step 17 can be perpendicular to the inner surface of the inner tube 14.

The arrangement 1 as shown in FIG. 1 is pre-assembled and comprises a pre-formed part, a connector part 21. The connector part 21 can be transformed into a functional element of the coupling 3 and surrounds a first outer surface 23 of the first fluid conduit 5 and a second outer surface 25 of the second fluid conduit 7. The connector part can realize, for example, a press fit with the first outer surface 23 and a loose fit with the second outer surface 25 of the second fluid conduit 7. Therefore, the arrangement 1 can comprise a gap between the connector part 21 and the second outer surface 25 of the second fluid conduit 7. The connector part 21 comprises a plastic material, for example, a thermoplastic material, for example, PEEK or PFA. The plastic material is adapted for being formed with a forming tool 29 comprising a cone-shaped mold 31. The mold 31 comprises an inner surface 32.

The forming tool 29 is cylindrically shaped and comprises an inner multiple-step bore 33 comprising a step 35. Behind the step 35, the multiple-step bore 33 realizes a gap 37 between the outer surface of the second fluid conduit 7 and the inner surface of the multiple-step bore 33. The gap 37 can be used, for example, for degassing the forming tool 29. For closing the forming tool 29, it can be moved coaxially in direction of the fluid conduits 5 and 7—in the direction of FIG. 1—from the right hand side to the left hand side, as indicated with an arrow 39. The connector part 29 is cylindrically shaped with an inner multiple-step bore 41 adapted for surrounding the first outer surface 23 of the first conduit 5 and the second outer surface 25 of the second conduit 7 and realizing the gap 27. In further embodiments, for realizing special features as undercuts or grained surfaces, the forming tool 29 can comprise two or more separable—not illustrated—tooling parts, for example, two mirror symmetrical tooling parts.

Figure 2:
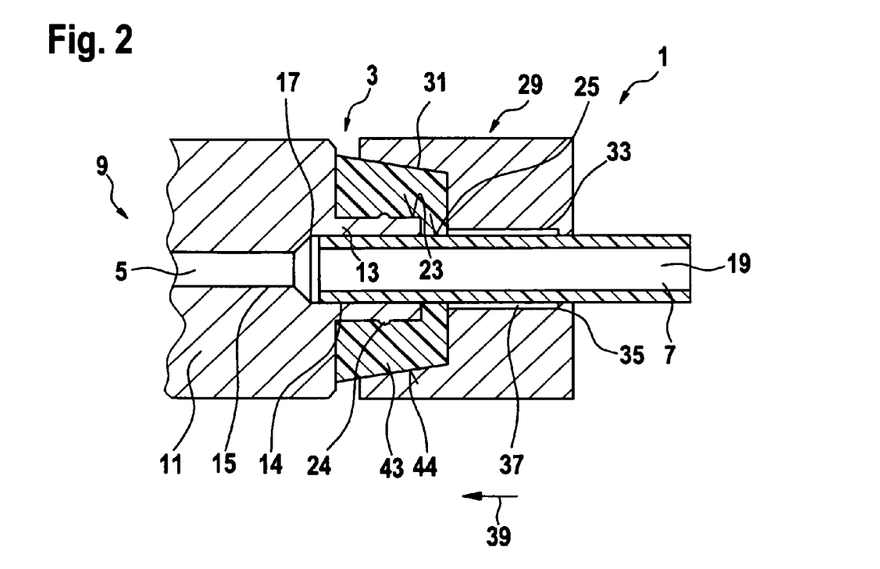
FIG. 2 shows a longitudinal view of the arrangement of FIG. 1, but with the closed forming tool.

FIG. 2 shows a longitudinal view of the arrangement 1 of FIG. 1, but with the closed forming tool 29. After closing the forming tool 29, the connector part 21 is transformed into the functional element, a connector 43 for the conduits 5 and 7, wherein the connector 43 is in a sealing contact with the outer surfaces 23 and 25 of the conduits 5 and 7. The outer surface 23 of the sheathing 13 and/or the outer surface 25 of the conduit can comprise at least one negative and/or at least one positive bead—as exemplarily shown as one positive bead 24 in FIG. 6—for improving the said sealing contact in a form-closed manner.

The outer surfaces 23 and 25 of the fluid conduits 5 and 7 are adjacent to each other and completely surrounded by the connector 43 at the interface. The already formed connector 43 comprises an outer cone-shaped surface 44 according the inner surface 32 of the cone-shaped mold 31 of the forming tool 29. The inner surface 32 of the mold 31 can be grained, wherein the outer surface 44 of the connector 43 is grained accordingly. The surface structure of the grained outer surface 44 realizes a plurality of micro resilient elements for adjusting any tolerances. Advantageously, the connector 43 can be fitted with an according not shown fitting, wherein the micro resilient elements of the outer surface 44 can adjust any tolerances of the not shown fitting and the connector 43.

For forming the connector 43, the plastic material of the connector part 21 can be plastified, for example, by heating, before moving the forming tool 29 from the right hand side to the left hand side—as illustrated in FIGS. 1 and 2. The plastified plastic material of the connector part 21 can easily be transformed into the cone-shaped connector 43 by exerting pressure into the plastic material with the forming tool 29. Possibly, the plastic material can be heated within the forming tool 29, wherein the plastic material expands and produces the pressure. As can be seen in FIG. 2, the gap 27 is closed completely after the step of forming.

In other embodiments, the plastic material of the connector 43 can be melted completely and afterwards cooled down to ambient temperature. Therefore, the plastic material can realize a chemical bond with the outer surfaces 23 and 25 of the conduits 5 and 7. Besides this, the plastic material of the connector 43 can be melted at least partly, for example by running a hot fluid through the conduits 5 and 7 for melting the plastic material at an interfacial area of the outer surfaces 23 and 25 of the conduits 5 and 7 and the connector part 43. This leads to the same advantageous chemical bond and to a permanent fixing of the two conduits 5 and 7. In other words, the conduits 5 and 7 are fixed with each other and sealed via the connector 43.

As an additional positive effect, the plastic material of the connector 43 can shrink on the outer surfaces 25 and 23 of the conduits 5 and 7. Therefore, the materials of the conduits 5 and 7 can comprise a lower thermal expansion than the plastic material of the connector 43. An advantageous combination is, for example, PEEK for the connector 43 and glass and/or metal for the conduits.

Figure 3:
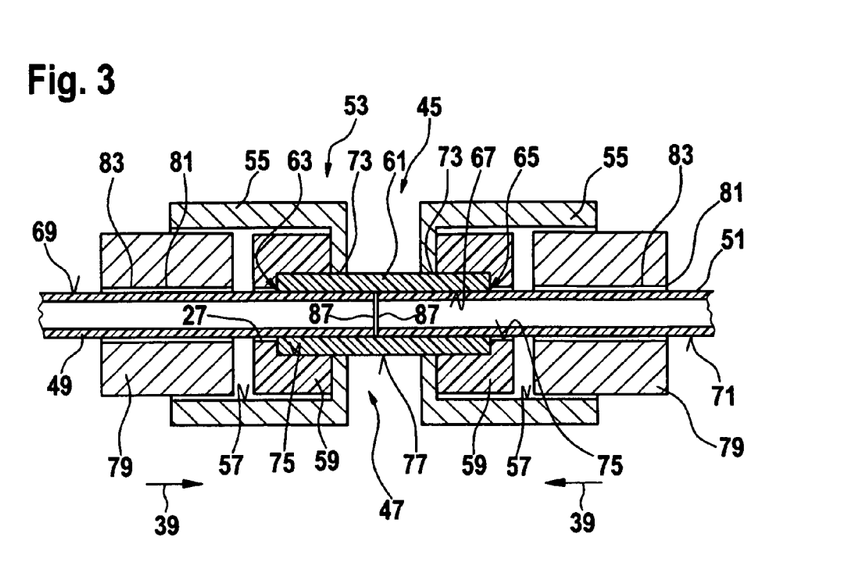
FIG. 3 shows a longitudinal view of an arrangement of a coupling for two conduits comprising the same diameter, with a sleeve together with a forming tool comprising two molds.

FIG. 3 shows a longitudinal view of a pre-assembled arrangement 45 of a coupling 47 adapted for connecting a first fluid conduit 49 with a second fluid conduit 51, wherein the outer diameters of the fluid conduits 49 and 51 are equal. The pre-assembled coupling 47 is shown in FIG. 3 together with a forming tool 53 adapted for fabricating the coupling 47. The forming tool 53 and the coupling 47 are designed symmetrically. Therefore, just the left hand side is described in detail. Parts being symmetrical to each other with the same function are referred to with the same reference sign.

The forming tool 53 comprises two outer cylindrically shaped forming parts 55 each comprising a mold 57. The molds 57 are cylindrically shaped and adapted for receiving and forming two connector parts 59. The connector parts 59 are shaped also cylindrically and adapted to be transformed into functional elements of the coupling 47. The coupling 47 comprises a sleeve 61 adapted for receiving the first and second conduits 49 and 51, wherein the conduits 49 and 51 can be inserted into a first opening 63 and a second opening 65 of the sleeve 61. The sleeve 61 comprises an inner surface 67 adapted for receiving the outer surfaces 69 and 71 of the conduits 49 and 51. The sleeve 61 can, for example, realize a press fit or a loose fit with the conduits 49 and 51. Advantageously, a slightly press fit within the sleeve 61 can be useful for pre-assembling the conduits 49 and 51. The outer forming parts 55 comprises a bore 73 adapted for receiving the sleeve 61 of the coupling 47. The sleeve 61 is inserted at least partly into the bore 73 of the outer forming part 55. Besides this, the connector part 59 is inserted into the cylindrically shaped mold 57 of the outer forming part 55 of the forming tool 53. The connector part 59 comprises an inner multiple-step bore 75 adapted for surrounding closely an outer surface 77 of the sleeve 61 and the outer surfaces 69 of the first fluid conduit 49.

Figure 4:
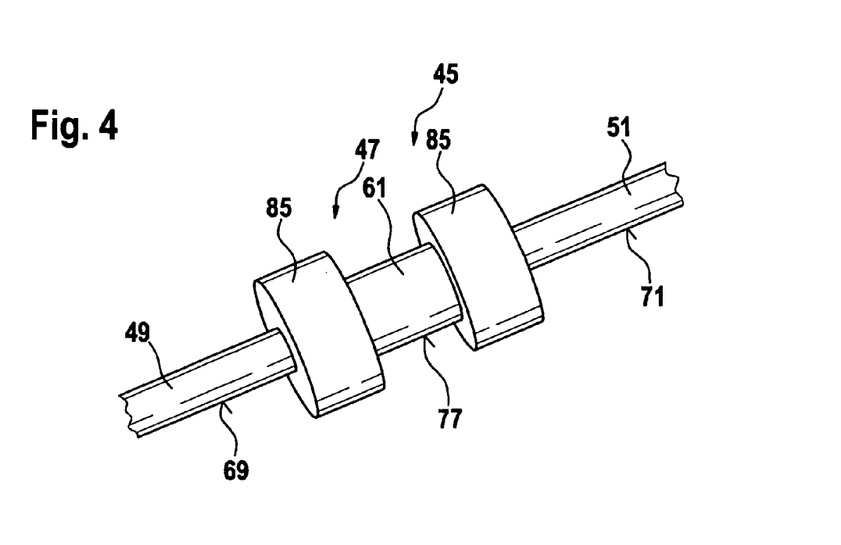
FIG. 4 shows a three-dimensional view of the arrangement of FIG. 3 completely fabricated and without the forming tool.

The forming tool 53 comprises two cylindrically shaped pistons 79 each comprising a bore 81 adapted for surrounding the outer surfaces 69 of the conduits 49 and 51 and for realizing gaps 83 adapted for degassing the molds 57 of the forming tool 53. For closing the forming tool 53, the piston 79 can be moved, in direction of FIG. 3, from the left hand side to the right hand side as indicated by the arrow 39. Therefore, the piston 79 can be moved into the mold 57 of the outer forming part 55 of the forming tool 53. The piston 79 can exert pressure to the plastic material of the connector part 59 for transforming it into a connector 85, as shown in FIG. 4. For demolding, the outer forming part 55 of the forming tool 53 has to be bipartite—not illustrated—and comprises at least two separatable parts.

The conduits 49 and 51 each comprise an outlet 87 facing each other. After transforming the connector part 59 into the connector 85, the outlets 87 of the conduits 49 and 51 are in communication with each other and are sealed via the sleeve and the connectors 85.

FIG. 4 shows a three-dimensional view of the arrangement 45 of the coupling 47 as shown in FIG. 3, but with already transformed connector parts, consequently with two connectors 85 surrounding each at least partly the outer surface 77 of the sleeve 61 and surrounding at least partly the outer surfaces 69 and 71 of the first conduit 49 and the second conduit 51. The first conduit 49 and the second conduit 51 are connected permanently by the two connectors 85 and the sleeve 61. The connectors 85 are shaped cylindrically, according to the inner shapes of the molds 57 of the forming tool 53 of the two molds 57 of the forming tool 53.

Figure 5:
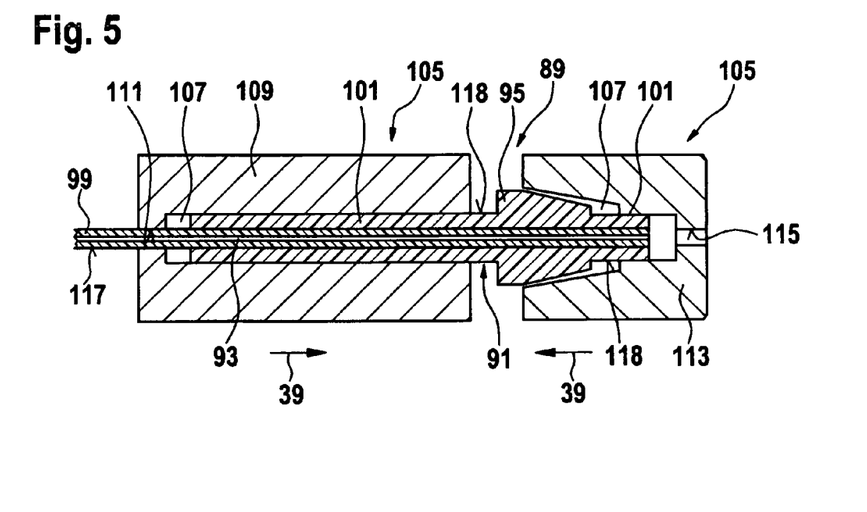
FIG. 5 shows a longitudinal view of a pre-fabricated arrangement of a coupling with a fitting part and one conduit surrounded with the fitting part in a partly closed forming tool.
Figure 6:
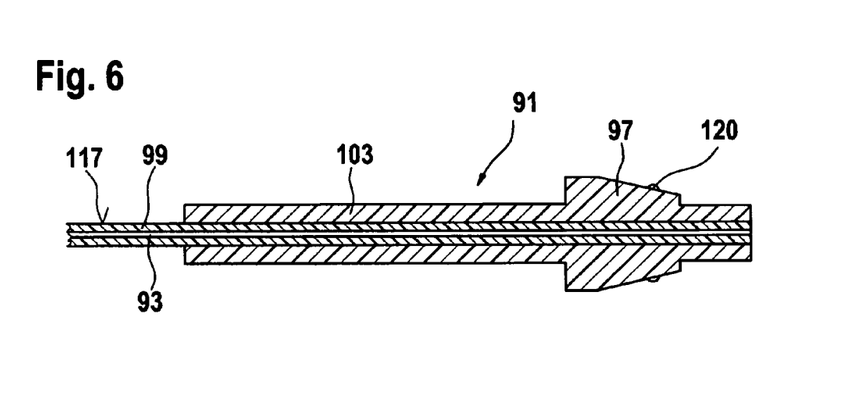
FIG. 6 shows a longitudinal view of the arrangement of FIG. 5 in a longitudinal view completely fabricated, but without the forming tool.

FIG. 5 shows a longitudinal view of a prefabricated arrangement 89 of a coupling 91 for a fluid conduit 93, for example a glass capillary. The fluid conduit 93 is surrounded by a pre-fabricated fitting part 95. The fitting part 95 can be transformed into a fitting 97, as shown in FIG. 6, for connecting the fluid conduit 93 with an other fluid conduit, for example a fluid conduit within an analytical arrangement for analyzing a liquid. The fluid conduit 93 comprises an inner tube 99. Besides this, the fitting part 95 comprises a cylindrically shaped extension 101 adapted for realizing a coating 103 of the fluid conduit 93 as shown in FIG. 6.

For transforming the fitting part 95 to the fitting 97 and the coating 103, the fitting part 95 is inserted together with the fluid conduit 93 into a forming tool 105. The fitting part 95 is inserted together with the fluid conduit 93 into molds 107 of the forming tool 105. The fluid conduit 93 is already surrounded by the fitting part 95. The forming tool 105 comprises a first forming part 109 comprising an inner multiple-step bore 111 and a second forming part 113 comprising an inner multiple-step bore 115 leading into a cone shaped span of the mold 107. The inner multiple-step bores 111 and 115 are adapted for surrounding exactly an outer surface 117 of the fluid conduit 93 and an outer surface 118 of the extensions 101 of the fitting part 95. The conically shaped span of the mold 107 of the second forming part 113 of the forming tool 105 is adapted for forming the conically shaped fitting 97 of the coupling 91. The forming tool 105 can comprise two or more separatable forming parts.

In embodiments, the fitting 97 as shown in FIG. 6 can comprise a sealing coating, for example silicon, rubber, Teflon®, or alike for sealing the fitting with an according receiving part for coupling the fluid conduit 93 with another conduit. In further embodiments, the fitting 97 can comprise an additional part, for example a gold ring 120—as shown in FIG. 6—which can be positioned within the tool prior to the forming process and can be fixed to the fitting by the forming process. After the forming process, the additional part is coupled to the fitting. Advantageously, the additional part has a better property than the plastic material itself, for example better sealing properties, depending on the sealing counterpart. The inner surfaces of the molds 107 can be grained at least partly, wherein the outer surface of the fitting 97 is grained at least partly accordingly after the step of forming the pre-fabricated fitting part 95 by the forming tool 105. Besides this, a current can be induced within the gold ring 120 for heating the plastic material within the forming tool. In further embodiments, the fitting can comprise a not shown thread for connecting the fitting with an according counter part.

For closing the forming tool, the first forming part 109 can be moved—in direction of FIG. 5—from the left hand side to the right hand side and the second forming part 113 can be moved—in direction of FIG. 5—from the right hand side to the left hand side, as indicated with the arrows 39. FIG. 6 shows a longitudinal view of the completely fabricated coupling 91 comprising the fitting 97 and the coating 103 surrounding the fluid conduit 93.

Figure 7:
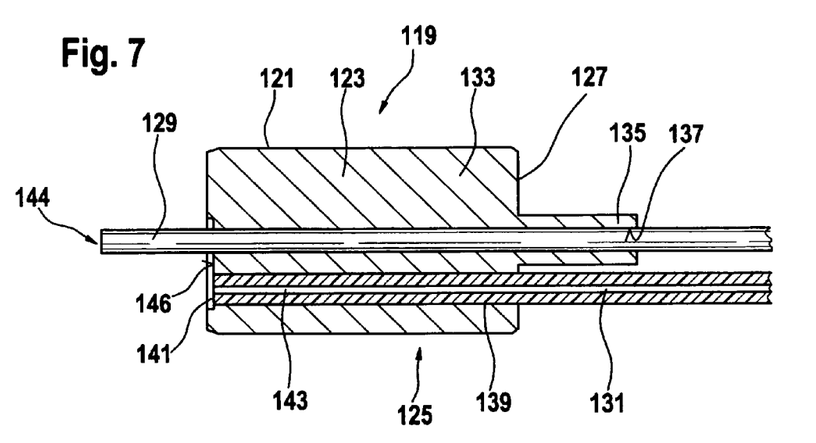
FIG. 7 shows a longitudinal view of a further arrangement of a coupling with a connector, a fluid conduit and a light guide comprising an optical fiber.

FIG. 7 shows a longitudinal view of an arrangement 119 with a coupling 121 comprising a connector 123. The connector 123 comprises a PEEK ferrule 125 and is cylindrically shaped with one step 127. The coupling 121 is adapted for connecting a light guide 129 and a fluid conduit 131, for example, a capillary, for example, a glass or fused silica capillary. The connector 123 comprises a cylindrically span with a greater diameter realizing a body 133 of the connector 123. Another span with a lower diameter realizes a coating 135 adapted for protecting the light guide 129 at least partly.

The connector 123 or better the PEEK ferrule 125 comprises a first inner bore 137 adapted for receiving the light guide 129 and comprises a second inner bore 139 adapted for receiving the fluid conduit 131. The first inner bore 137 is realized as a centric bore and the second inner bore 139 is a bore in the periphery of the body 133. The two inner bores 137 and 139 are arranged parallel to each other.

The body 133 of the connector 123 comprises at the opposite side of the coating 135 a recess 141. Both inner bores 137 and 139 of the connector 123 lead into said recess 141. An inner tube 143 of the fluid conduit leads into the recess 141 of the connector 123. The outlet of the fluid conduit 131 is installed flush with the recess 141 and the light guide 129 projects the recess 141. The coupling 121 can be used, for example, for connecting or for bringing the fluid conduit 131 and the light guide 137 in communication with each other. Therefore, the connector 123 of the coupling 121 can be connected with a flow cell. Therefore, the inner tube 143 and the recess 141 leads into a fluid conduit of the flow cell—in direction of FIG. 7—on the left hand side of the coupling 121. The fluid conduit or better the cell of the not shown flow cell can be irradiated by an optical outlet 144 of the light guide 129 projecting into said not shown flow cell.

Figure 8:
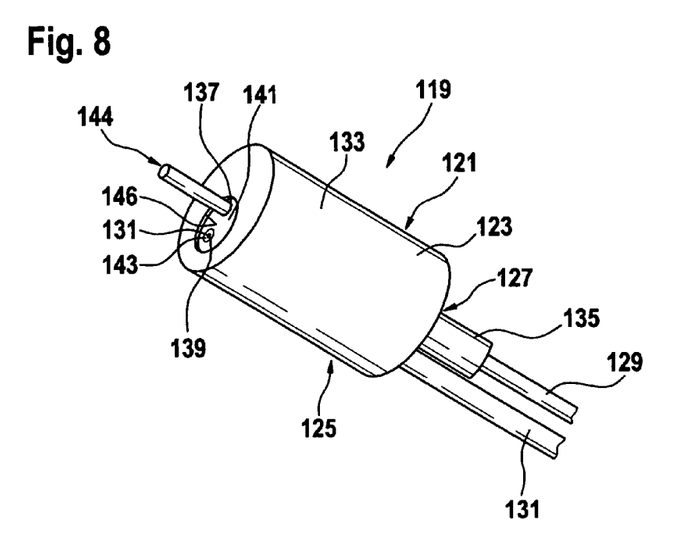
FIG. 8 shows a three-dimensional view of the arrangement of FIG. 7.

FIG. 8 shows a three-dimensional view of the arrangement 119 with the coupling 123. Visible is the recess 141, comprising the inner bores 137 and 139 of the body 133 of the connector 123 of the coupling 121. The fluid conduit 131 ends flush with a surface 146 of the recess 141 or can slightly intersect the surface 146, wherein the light guide 129 intersects the surface 146 of the recess 141 and overlaps it. In further embodiments, the light guide 129 can be flush-mounted into the connector 123. For uncovering the light guide 129, the surface 146 of the recess 141 can be grinded, machined, and/or milled off until the light guide 129 gets visible. Thereafter, the optical outlet of the light guide 129 can be polished.

Figure 9:
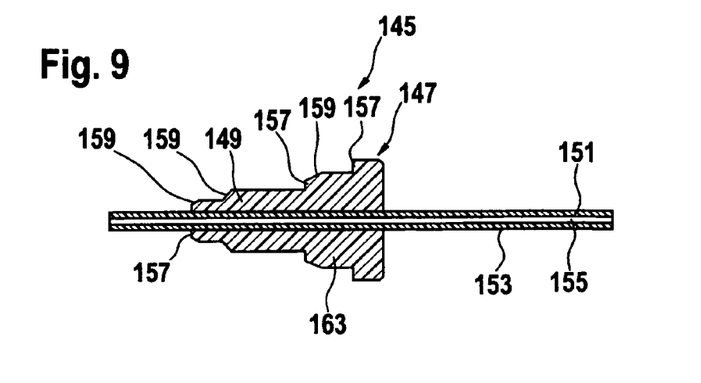
FIG. 9 shows an arrangement of a further coupling with a fluid conduit provided with a fitting.
Figure 10:
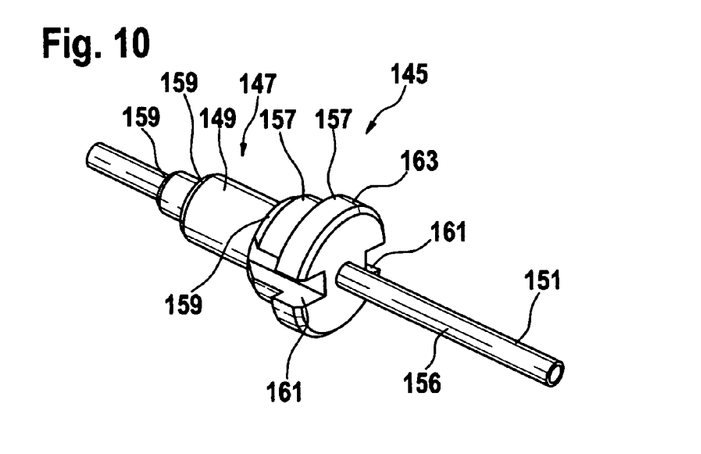
FIG. 10 shows a three dimensional view of the arrangement of FIG. 9.
Figure 11:
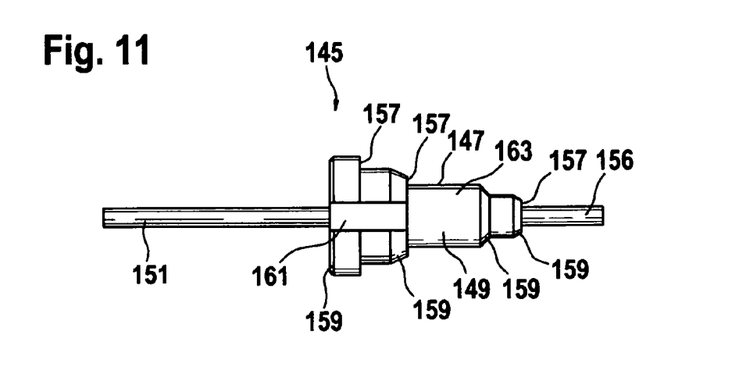
FIG. 11 shows a side view of the arrangement of FIG. 9, but with a light guide instead of the fluid conduit, comprising an optical fiber.

FIG. 9 to 11 show different views of an arrangement 145 of a coupling 147 with a fitting 149. The fitting 149 surrounds a conduit 151. The conduit 151 can be realized as a capillary 153 comprising an inner tube 155 or as a light guide 156. In the longitudinal view of FIG. 9, the arrangement 145 is shown with the capillary 153. The fitting 149 of the coupling 147 is substantially cylindrically shaped with a variety of steps 157 and chamfers 159. The steps 157 and chamfers 159 of the fitting 149 reduce the outer diameter of the fitting 149—in direction of FIG. 9—towards the left hand side. Therefore, the fitting 149 can be plugged into an (not shown) according connector. For adjusting the fitting 149, the conduit 151 can be cut off and polished thereafter.

Figure 12:
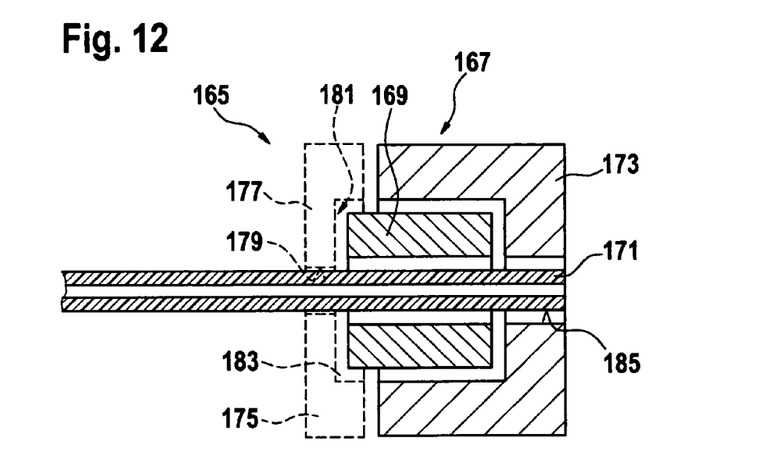
FIG. 12 shows a longitudinal schematic view of a pre-fabricated arrangement of a coupling with a fitting part and one conduit surrounded with the fitting part and an additional housing part together with a forming tool.

FIG. 10 shows the arrangement comprising the light guide 156 in a three-dimensional view, and FIG. 11 in a side view. The fitting 149 comprises two grooves 161. The grooves 161 are in an opposed mounting and inserted in parallel in a span of a body 163 of the fitting 149. The grooves 161 are adapted for guiding the coupling 147 within the according female connector adapted for receiving the fitting 149 and can, for example, avoid an undesired rotation of the coupling 147 within the female connector. The fitting 149 as shown in Fig FIG. 12 shows a longitudinal schematic view of a prefabricated arrangement 165 of a coupling 167 with a pre-formed fitting part 169 and one conduit 171 surrounded with the fitting part 169 and an additional housing part 173 together with a forming tool 175. The conduit 171 can be realized as a quartz capillary. The fitting part 169 can be transformed by the forming tool 175 to a functional element, a sealing part. The forming tool 175 comprises a round washer 177 with a centric bore 179 and a centric circular recess 181. The recess 181 of the forming tool realizes a mold 183 of the forming tool 175. For forming the fitting part 169, the forming tool 175 can be moved—in direction of FIG. 12—from the left hand side to the right hand side for exerting pressure on the fitting part 169. Concurrently, the fitting part 169 can be plastified, for example, by heating. The fitting part 169 surrounds at least partly an outer surface 185 close to the end of the conduit 171. The fitting part 169 is surrounded at least partly by the additional housing part 173 and by the recess 181 of the mold 183 of the closed forming tool 175. In embodiments, the housing part 173 is fixed with the conduit 171 via the transformed fitting part 169. The coupling comprises the transformed fitting part 169 and the housing part 173. In other embodiments, it is possible, that the transformed fitting part 169 shrinks after the step of transforming on the outer surface 171 of the conduit 175. Dependent on the thickness of the transformed fitting part 169, the contact of the fitting part 169 with an inner surface of the housing part 173 can be released by the step of cooling the transformed fitting part 169. This makes it possible to remove the housing part 173 also.

Figure 13:
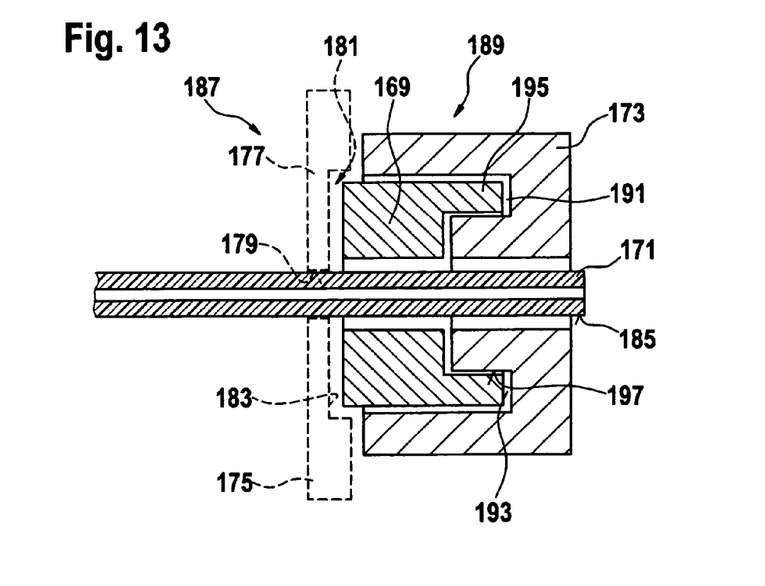
FIG. 13 shows a longitudinal schematic view of another pre-fabricated arrangement of a coupling with a fitting part and one conduit surrounded with the fitting part and an additional housing part together with a forming tool, wherein the housing part comprises an undercut.

FIG. 13 shows a longitudinal schematic view of another pre-fabricated arrangement 187 of a coupling 189. In difference to the arrangement 165 of FIG. 12, the housing part 173 of the arrangement 187—as shown in FIG. 13—comprises an undercut 191 realizing a circular groove 193. The fitting part 169 of the arrangement 187 comprises a circular rib 195 projecting into the groove 193 of the housing part 173. The housing part 173 or rather the groove 193 of the arrangement 187 comprises an outer surface 197. Advantageously, for sealing the housing part 173 and the conduit 171, the fitting part 169 can shrink after the step of forming on the outer surface 185 of the conduit 171 and on the outer surface 197 of the housing part 173. By this, the housing part 173 can be fixed fluid tight with the conduit 171 by the transformed fitting part. The housing part can comprise a fitting, for example, a standardized fitting, for example, a thread, a male or female part of a plug-and-socket device, and/or alike.

Figure 14:
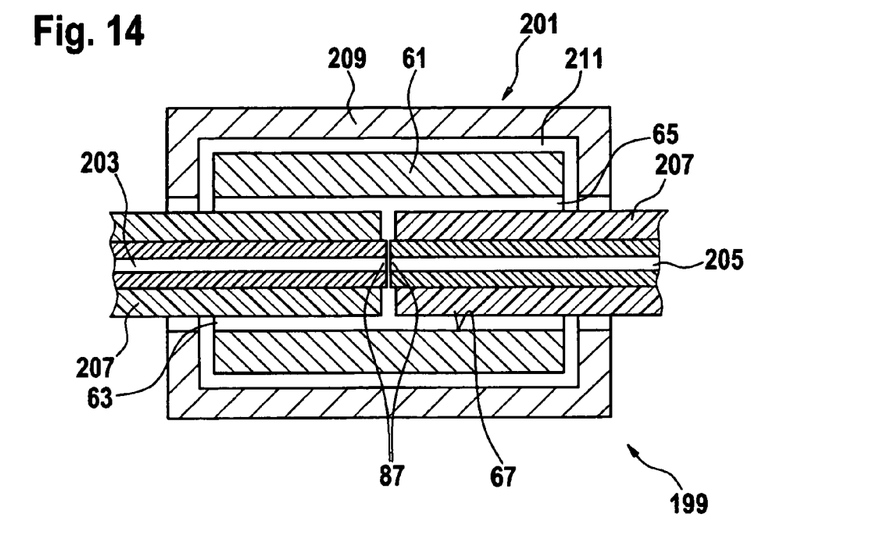
FIG. 14 shows a schematic longitudinal view of another arrangement of a coupling for two conduits comprising a coating, with a sleeve and a single-use forming tool with one mold.

FIG. 14 shows a schematic longitudinal view of another arrangement 199 of a coupling 201 for two conduits 203 and 205 each comprising a coating 207. The arrangement 199 comprises a sleeve or fitting part 61 and a single-use forming tool 209 with one mold 211. The conduits 203 and 205 can be realized as steel or quartz capillaries coated with PEEK or FEP. The single-use forming tool 209 can comprise two tooling parts that can be fixed with each other. For fixing the conduits 203 and 205 with each other, the coatings 207 can be plastified within the mold 211 of the forming tool 209, for example, by inducing a current in the sleeve 61. For this purpose, the sleeve 61 comprises a conductive material, for example, steel. Due to the forming tool 209, the expanding plastic material within the sleeve 61 cannot escape. Consequently, pressure builds up within the sleeve 61. Advantageously, the forming tool 209 can comprise a non-conductive material and remains cool while heating up the sleeve 61 by inducing a current. Advantageously, the coatings 207 close to the forming tool 209 remain cool also. Consequently, the forming tool cannot cling to the outer surfaces of the conduits 203 and 205.

The forming tool 209 can comprise two tooling parts fixed with each other. After plastifying and cooling down the coatings 207, the conduits 203 and 207 are fixed with each other via the sleeve 61, more precisely, the coatings 207 are adhesive-bonded and/or chemically compounded or mechanically interlinked with the inner surface 67 of the sleeve 61. The coatings 207 of the ends of the conduits 203 and 205 realize functional elements of the coupling 201 adapted for fixing the conduits with each other via the sleeve 61. More precisely, the coating 207 of the end of the first conduit 203 is fixed with the second conduit 205 via the sleeve 61 and the coating 207 of the end of the second conduit 205 is fixed with the first conduit 203 via the sleeve 61. Advantageously, the forming tool 209 can remain at the coupling 201. The forming tool 209 can comprise ceramic materials. In other embodiments, the forming tool 209 can be opened, removed, and used again for producing a further coupling. The forming tool 209 does not cling at the outer surface of the sleeve 61.

In further embodiments, the forming tool 209 can be used together with a sleeve 61 comprising PEEK or FEP. Besides this, such a combination can be used together with conduits, for example, steel or quartz capillaries without coating. The inner surface 67 can comprise the PEEK or FEP for realizing the connection with the outer surfaces of the conduits. The sleeve 61 can be transformed to a connector within the mold 211 of the forming tool 209.

Figure 15:
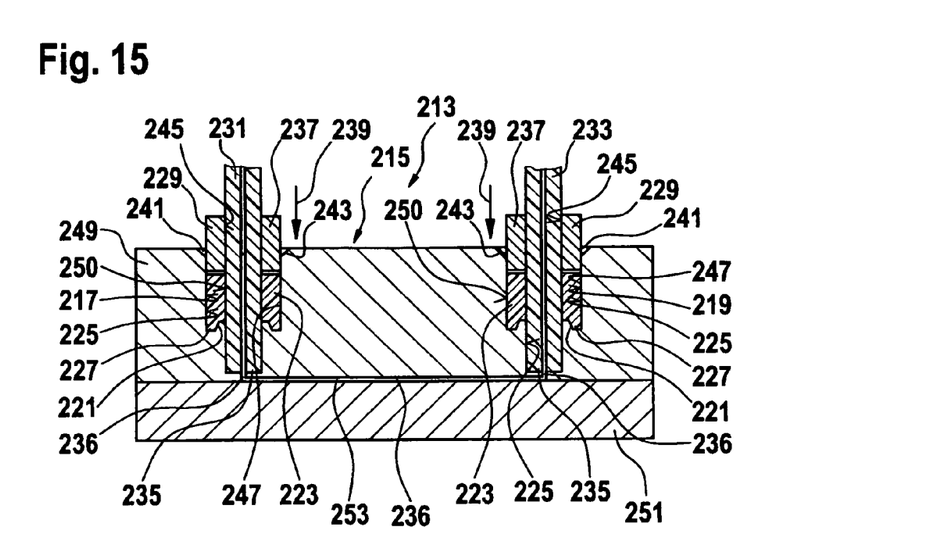
FIG. 15 shows a cross-sectional view of an arrangement of a coupling with a first multiple-step bore and a second multiple-step bore each comprising an undercut surrounded with the plastic material of a sealing part.
Figure 16:
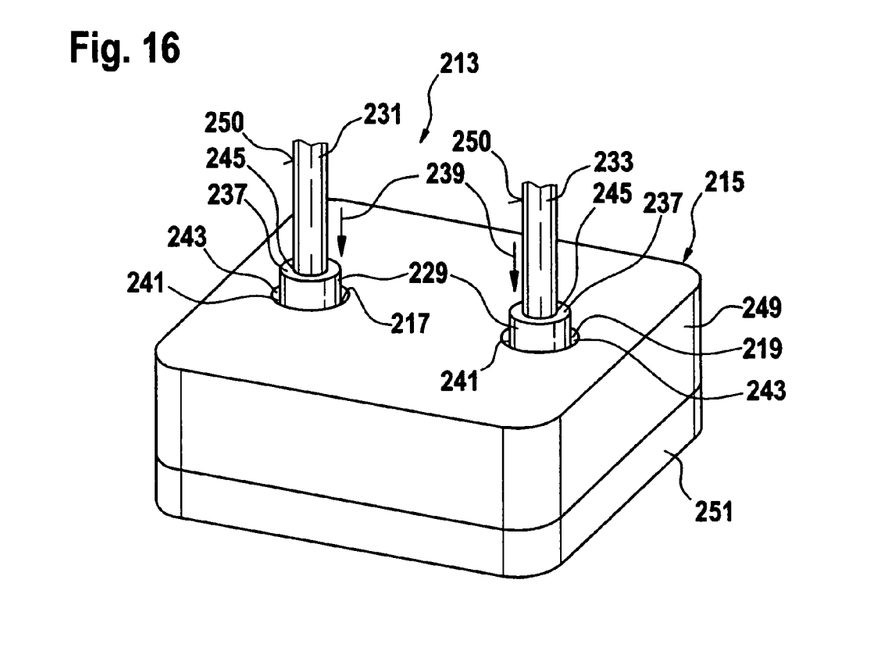
FIG. 16 shows a three-dimensional top front side view of the arrangement of FIG. 15.

FIG. 15 shows a cross-sectional view of an arrangement 213 of a coupling 215 with a first multiple-step bore 217 and a second multiple-step bore 219 each comprising an undercut 221 surrounded with the plastic material of a sealing part 223. FIG. 16 shows a three-dimensional top front side view of the arrangement 213 of FIG. 15. The undercuts 221 are within the multiple-step bores 217 and 219 and are part of an inner surface 225 of the multiple-step bores 217 and 219. The multiple-step bores 217 and 219 each comprise a step 227 comprising the undercuts 221. For producing the coupling 215, the plastic material of the sealing parts 223 can be inserted together with a first conduit 231 and a second conduit 233 into the first multiple-step bore 217 and the second multiple-step bore 219. The conduits 231 and 233 each are limited at a step 235 of the multiple-step bores 217 and 219. The multiple-step bores 217 and 219 narrow at the step 235 to the diameter of a connecting conduit 236 of the coupling 215. The plastic material of the sealing parts 223 are encapsulated by a forming tool 229 for exerting pressure and for forming the sealing parts 223 within the multiple-step bores 217 and 219. The forming tools 229 each comprise a simple sheathing 237 surrounding the conduits 231 and 233. For forming the sealing parts, the plastic material can be plastified and/or melted and the sheathings 237 of the forming tools 229 can be moved—in direction of FIG. 15—downwards, as indicated by arrows 239.

The forming tool 229 is adapted for encapsulating the plastic material of the sealing parts 223 within the multiple-step bores 217 and 219. The thickness of the sealing parts 223 surrounding the conduits 231 and 233 is dimensioned so that the plastified and/or melted plastic material would flow out of the multiple-step bores 217 and 219 of the coupling 215 during the step of plastifying and/or melting. To avoid this, the forming tool 229 can be inserted additionally into openings 241 of the multiple-step bores 217 and 219 of the coupling 215 for enclosing or encapsulating the plastic material within the multiple-step bores 217 and 219. The multiple-step bores 217 and 219 each comprise a chamfer 243 for simplifying the step of inserting the conduits 231 and 233 and the pre-formed sealing parts 223. The sheathings 237 of the forming tools 229 each comprise a bore 245 adapted for receiving the conduits 231 and 233. After transforming the sealing parts 223, the forming tools 229 can be removed or can remain within the multiple-step bores 217 and 219. Advantageously, the inner surfaces 225 of the multiple-step bores 217 and 219 realize a part of molds 247 of the forming tool 229. After cooling down, the plastic material of the sealing parts 223 can shrink on outer surfaces 250 of the conduits 231 and 233 and the undercuts 221 of the inner surfaces 225 of the multiple-step bores 217 and 219.

The coupling 215 comprises a planar cover part 249 and a planer base plate 251 fixed with each other and comprising the connecting conduit 236. The connecting conduit 236 can be integrated in a groove 253 of the base plate 251 of the coupling 215. The groove 253 leads into the multiple-step bores 217 and 219 and consequently connects the conduits 231 and 233 via the multiple-step bores 217 and 219.

Figure 17:
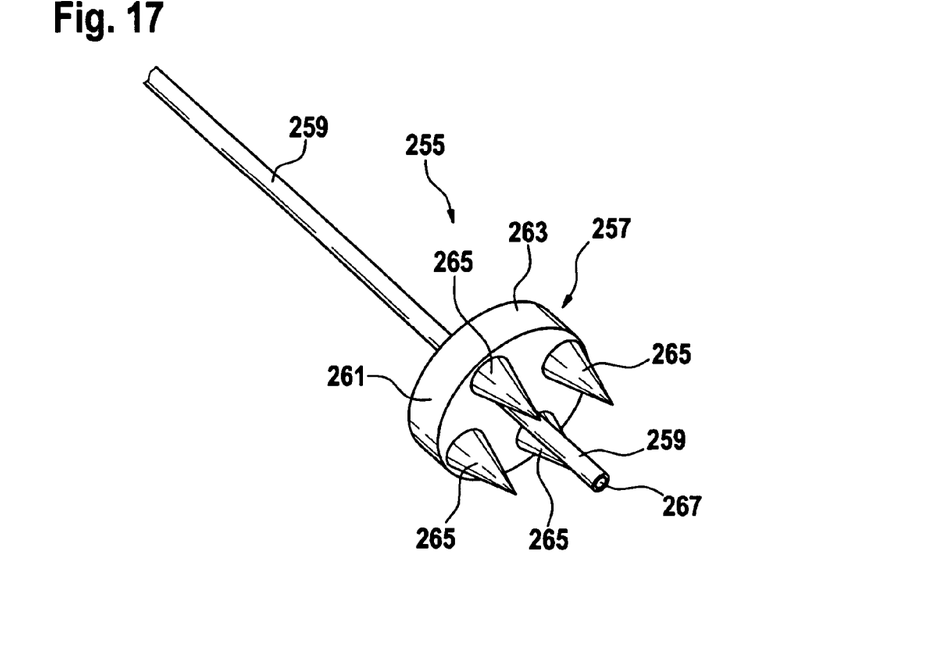
FIG. 17 shows an arrangement of a further coupling with a conduit provided with a fitting.

FIG. 17 shows an arrangement 255 of a coupling 257 with a conduit 259 provided with a fitting 261. The fitting 261 comprises a disk-shaped body 263 attached to the conduit 259 and shaped by a not shown forming tool. Besides this, the fitting 261 comprises four cone-shaped noses 265 extending coaxially to the axis of the conduit 259 towards an outlet 267 of the conduit 259. The cone-shaped noses 265 are adapted for aligning the fitting 261 and accordingly the conduit 259 in an according counter part.

In other embodiments, the forming tool can comprise a pair of tooling parts arranged similar as a pair of pliers. By this, it is possible to use the forming tool in practice in the field, for example, in a lab.

The separation column 9 and/or the not shown flow cell can be part of a fluid separation system comprising a fluid delivery system, a separation device adapted for separating components delivered by the fluid delivery system. The flow cell can be used for detecting the separated components within the fluid. The fluid separation system can comprise, for example, a chromatographic system (LC), a high performance liquid chromatographic (HPLC) system, an HPLC arrangement comprising a chip and an mass spectrograph (MS), a high throughput LC/IMS system, a purification system, micro fraction collection/spotting system, a system adapted for identifying proteins, a system comprising a GPC/SEC column, a nanoflow LC system, and/or a multidimensional LC system adapted for separation of protein digests.

The coupling can be used for analyzing liquid. More specifically, the coupling can be part of an apparatus, for example comprising a flow cell, adapted for executing at least one microfluidic process, for example a liquid chromatographic process, for example a high performance liquid chromatographic process (HPLC). Therefore, the flow cell can be coupled to a liquid delivery system, in particular to a pump, and/or to a power source and/or to a detection system, for example, a light detector. For analyzing liquid or rather one or more components within the liquid, the flow cell can comprise a detection area, such as an optical detection area and/or an electrical detection area being arranged close to or in a flow path within the flow cell. Besides this, the flow cell can be a component part of a laboratory arrangement.

In the following, a method of providing conduits with at least one functional element is described in detail by referring to the FIG. above, in particular to the FIGS. 1 and 2.

The functional element is adapted for connecting, sealing, positioning, receiving, fixing, adjusting, aligning, and/or protecting the conduits. The conduits are adapted for conducting a medium, for example, a fluid (gas or liquid), for example a liquid solvent comprising a sample and/or light, for example, UV light.

The pre-fabricated or pre-formed connector part 21 is plastified and molded within the forming tool 29. The forming tool is made of a hard durable material for example like metal, stainless steel or ceramics in order to be able to receive the forces of the forming process. The forming tool can comprise multiple parts and is adapted for shaping the form of the functional element and for attaching the functional element to the conduit.

In embodiments, firstly, the forming tool 29 is loaded with at least one conduit, for example, a fluid conduit, the second fluid conduit 7. Advantageously, as shown in FIG. 1, the forming tool 29 can be loaded just with the second fluid conduit 7. In other embodiments, the forming tool 29 can be loaded with the first fluid conduit 5 and with the second fluid conduit 7.

For example, the plastic material of the pre-formed connector part 21 can be plastified before closing the forming tool 29. In other embodiments, it is possible to plastify the plastic material of the connector part 21 after closing the forming tool. In other embodiments, it is possible, to heat the plastic material 21 to a first temperature below the softening point and then to close the forming tool and to heat to a second higher temperature above the softening point for plastifying the plastic material after closing the forming tool. After transforming the connector part into the connector 43, the already formed connector 43 can be cooled down to ambient temperature. This step can be executed before and/or after opening the forming tool 29.

In a further step, the forming tool 29 can be removed from the conduits 5 and 7. Therefore, the forming tool 29 can comprise two separable tooling parts, for example, two mirror symmetrical tooling parts. For realizing special features as undercuts or grained surfaces, the forming tool can comprise more than two tooling parts. Advantageously, the plastic material of the pre-formed connector part 21 can be shrunk on the outer surfaces 23 and 25 of the conduits 5 and 7 by cooling it down to ambient temperature. In other embodiments, the plastic material can be heated at least partly at an interfacial area of the outer surfaces 23 and 25 above its melting temperature for realizing a chemical bond of the outer surfaces 23 and 25 with the plastic material of the completely fabricated connector 43. The frictional forces due to the shrinking process and/or the bonding force of the chemical bond fix the two conduits 5 and 7 with each other and seal them in a fluid tight manner. The contact zone can be melted at least partly by running a hot fluid or hot gas through the conduits 5 and 7. In other embodiments, the contact zone can be heated partly by an external heat source, for example, by an electrically heated spiral. Possibly, the contact zone can be heated above the melting temperature of the plastic material by inducing a current in the conduits 5 and 7. For this purpose, the conduits 5 and 7 may comprise a conductive material such as metal or a metal compound or coat.

As shown in FIG. 3, the forming tool 53 can comprise two molds 57 and two pistons 79 for exerting pressure to the connector parts 59. By exerting pressure to the pre-formed connector parts 59, the process of transforming the connector parts can be optimized, wherein the plastic material can penetrate the surface structure of the conduits and, for example, of the sleeve 61 adapted for receiving the ends of the conduits.

The method as described can be used for transforming a variety of different pre-fabricated parts, for example, for providing conduits with connectors, coatings, positioners and/or fittings, for example, standardized fittings. The functional elements are permanently fixed with the conduits after executing the method.

It is to be understood, that this invention is not limited to the particular component parts of the devices described or to process steps of the methods described as such devices and methods may vary. For example, all described conduits may comprise a coating. It is also to be understood, that different features as described in different embodiments, for example illustrated with different Figs., may be combined to new embodiments. It is finally to be understood, that the terminology used herein is for the purposes of describing particular embodiments only and it is not intended to be limiting. It must be noted, that as used in the specification and the appended claims, the singular forms of "a", "an", and "the" include plural referents until the context clearly dictates otherwise. Thus, for example, the reference to "a coupling", "a capillary", or "an inner surface" may include two or more such functional elements. The conduits, looking at the cross-section, may not only comprise round material as in this application noted, but also can be of any shape, for example, flat, triangle, square, oval, rectangle, hexagonal, and other, for example, for realizing misuse save couplings and/or fittings.

The invention claimed is:

1. A method of providing a conduit with a functional element, wherein the conduit is adapted for conducting a medium and comprises at least one of a group consisting of a capillary, a glass capillary, a fused silica capillary, a light guide, a single mode glass fiber, a mono mode glass fiber, a single polymer fiber, a mono mode polymer fiber, a fiber bundle, a liquid light guide, a refraction index modified capillary, and a photonic bandgap fiber, and wherein the functional element is adapted for at least one of: coupling, connecting, sealing, fixing, adjusting, aligning, receiving, protecting, and positioning the conduit, the method comprising:
loading a forming tool with at least one of: said conduit, a part of said conduit, an end of said conduit, and with a pre-formed part comprising a plastic material or compound,
changing a shape of the pre-formed part into the form of the functional element, by moving the forming tool coaxially along the conduit to directly contact and exert pressure on at least an end face of the pre-formed part, the end face extending along a plane perpendicular to a coaxial direction of the conduit,
plastifying and molding said pre-formed part within said forming tool for attaching the functional element to the conduit, and for coupling the conduit to another conduit, by heating said plastic material beyond a softening temperature of the plastic material for bringing it in its softening range and making it soft or beyond the softening temperature and at least partly above the melting temperature for melting said plastic material, and
opening the forming tool, by separating tool parts of the forming tool, after forming the functional element.

2. The method of claim 1, comprising:
surrounding an outer surface of the conduit at least partly with the pre-formed part adapted to the shape of the conduit and of the forming tool.

3. The method of claim 1, comprising at least one of:
exerting pressure on the plastic material caused by the thermal expansion of the plastic material by heating the closed forming tool comprising the plastic material, and
exerting pressure on the plastic material by closing the forming tool, actively cooling down the plastic material and/or the forming tool.

4. The method of claim 1, comprising at least one of:
shrinking the plastic material by cooling the plastic material down to ambient temperature;
shrinking the plastic material on the outer surface of the end of the conduit;
cooling the plastic material within the forming tool;
heating the plastic material within the forming tool above the melting temperature for melting the plastic material; and
heating the plastic material at least partly above the melting temperature for melting the plastic material at least partly.

5. The method of claim 1, comprising at least one of:
melting the plastic material at least partly at a contact zone at the end of the conduit and the plastic material,
melting the plastic material at least partly after molding it,
melting the plastic material at least partly after molding it and before opening the tool,
melting the plastic material at least partly after removing it from the tool,
running a hot fluid through the conduit for melting the plastic material at the contact zone;
equipping the end of the conduit with the pre-formed part before loading the forming tool.

6. The method of claim 1, wherein the pre-formed part comprises at least one of: a pre-formed fitting part, a pre-formed coating part, a pre-formed connector part, or wherein the forming tool comprises a first mold and a second mold, and wherein the pre-formed part plastic material comprises a first connector part and a second connector part, comprising:
molding the pre-formed part to the conduit for providing the conduit with at least one of:
a fitting adapted for coupling the conduit with e another conduit,
a coating adapted for protecting the conduit, and
a connector adapted for permanently connecting the conduit and the another conduit, or for providing the conduit and a sleeve with a first connector and the another conduit and the sleeve with a second connector.

7. The method of claim 6, comprising:
surrounding the outer surface of the conduit at least partly with at least one of: the pre-formed fitting, wherein the outer surface is adjacent to an outlet of the conduit, the pre-formed coating part, the pre-formed connector part, or surrounding an outer surface of the sleeve and the outer surfaces of the conduits at least partly with the first and second pre-formed connector parts.

8. The method of claim 6, comprising:
molding the pre-formed part to the conduit for providing the conduit with at least one of: a fitting adapted for coupling the conduits, a coating adapted for protecting the conduit, at least one connector adapted for permanently connecting the conduits.

9. The method of claim 6, comprising at least one of:
plastifying and molding the pre-formed fitting part within the forming tool for forming the fitting and for fixing the fitting with the conduit,
plastifying and molding the pre-formed coating part within the forming tool for forming the coating and for fixing the coating with the conduit,
plastifying and molding the pre-formed connector part within the forming tool for forming the connector and for fixing the connectors with the conduit, and
plastifying and molding the first connector part within the first mold and the second connector part within the second mold of the forming tool for forming the first and the second connector, for fixing the first connector with the conduit and the sleeve, and for fixing the second connector with the another conduit and the sleeve.

10. The method of claim 6, comprising at least one of:
loading the forming tool with the ends of the conduit and the another conduit and with the pre-formed connector part;
inserting the end of the conduit into an inner tube of the another conduit;
inserting the conduit into a first opening of the sleeve and inserting the another conduit into a second opening of the sleeve.

11. The method of claim 6, comprising at least one of:
surrounding an outer surface of the conduit and an outer surface of the another conduit with the at least one pre-formed connector part after inserting an end of the conduit into an inner tube of the another conduit, wherein the outer surfaces of the conduit and the another conduit are adjacent to each other;
surrounding the outer surface of the sleeve adjacent to the first opening with the first connector part and surrounding the outer surface of the sleeve adjacent to the second opening with the second connector part; and
surrounding the outer surface of the conduit and the sleeve at least partly with the first pre-formed connector part and surrounding the outer surface of the another conduit and the sleeve at least partly with the second pre-formed connector part, wherein the surrounded outer surface of the sleeve is adjacent to the surrounded outer surfaces of the conduits.

12. The method of claim 6, comprising at least one of:
loading the first mold with the conduit and loading the second mold with the another conduit;
loading the first mold with the first connector part and loading the second mold with the second connector part;
equipping the ends of the conduits with a sleeve; and
pre-connecting the conduits by inserting the ends of both conduits into the sleeve.

13. The method of claim 1, comprising at least one of:
the plastic material is at least one of: a thermoplastic material, polyetheretherketone, flouropolymeres, in particular perfluoroamines or flourinated ethylen-propylene copolymer, duroplastic material or compound, in particular polyimide, liquid crystal polymers; the medium is at least one of: light, a liquid, a gas; the conduit is at least one of: a capillary, in particular a liquid or a gas, a glass capillary, a fused silica capillary, a light guide, in particular single mode or monomode glass or polymer fibers, fiber bundles, liquid light guides, refraction index modified capillaries, photonic bandgap fibers, an analytical separation column, and an adapter design, in particular a bore in planar structure.

* * * * *